United States Patent [19]  [11] Patent Number: 4,687,845
Hollowood et al.                [45] Date of Patent: Aug. 18, 1987

[54] PREPARATION OF THIAZINE DERIVATIVES

[75] Inventors: John Hollowood, York; Arthur Jackson, Washington; Graham Heyes, Durham, all of England

[73] Assignee: Fine Organics Limited, Middlesbrough, England

[21] Appl. No.: 818,271

[22] Filed: Jan. 13, 1986

[30] Foreign Application Priority Data

Jan. 14, 1985 [GB] United Kingdom ............... 8500863

[51] Int. Cl.$^4$ ........................................... C07D 279/06
[52] U.S. Cl. ......................................... 544/54; 544/53
[58] Field of Search .................................. 544/53, 54

[56] References Cited

U.S. PATENT DOCUMENTS 3,993,648 11/1976 Powell .................................. 544/53
4,061,749 12/1977 Powell .................................. 544/53

Primary Examiner—Henry R. Jiles
Assistant Examiner—J. G. Mullins
Attorney, Agent, or Firm—Bert J. Lewen; Henry Sternberg

[57] ABSTRACT

A method for the preparation of a thiazine derivative, having insecticidal properties, of the formula

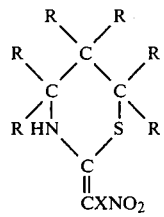

where each R is hydrogen or an appropriate aromatic or aliphatic substituent and X is hydrogen, halogen or lower alkyl, the method comprising reacting together a sulphur donor, a compound of the formula $Y_2C=CX-NO_2$ where Y is halogen (preferably chlorine) or another appropriate leaving group and a compound of the formula $$H_2NCR_2CR_2CR_2OSO_3H.$$

8 Claims, No Drawings

PREPARATION OF THIAZINE DERIVATIVES

This invention relates to methods of preparing thiazine derivatives which have insecticidal activity.

Tetrahydro-2-(nitromethylene)-2H-1,3-thiazine (I) possesses broad spectrum insecticidal activity, being particularly active against lepidopterous larvae on plants. It is also useful as an intermediate in the synthesis of more stable but equally active insecticides e.g., the oxime of 5,6-dihydro-4H-1,3-thiazine-2-carboxaldehyde (II).

The two known synthetic methods for preparing compound I are outlined below:

Route A $$\overset{\ominus\,\oplus}{Cl NH_3 CH_2 CH_2 CH_2 SH} + (CH_3S)_2C=CHNO_2 \xrightarrow{aq.\ NaOH}$$

Route B $$HN\underset{\underset{S}{\|}}{\diagup\!\!\!\diagdown}S + (CH_3)_2SO_4 \longrightarrow N\underset{\underset{SCH_3}{\|}}{\diagup\!\!\!\diagdown}S + ZnCl_2 +$$

$$\underset{CO_2Et}{\overset{CH_2NO_2}{|}} \longrightarrow HN\underset{\underset{O_2N\ \ CO_2Et}{C}}{\diagup\!\!\!\diagdown}S \xrightarrow[\text{(ii) HOAc}]{\text{(i) NaOH}} HN\underset{\underset{CHNO_2}{\|}}{\diagup\!\!\!\diagdown}S$$

Route C $$\overset{\ominus\,\oplus}{Cl NH_3(CH_2)_3SH} + Cl_2C=CHNO_2 \xrightarrow{aq.\ NaOH} HN\underset{\underset{CHNO_2}{\|}}{\diagup\!\!\!\diagdown}S$$

Routes A and C suffer from the disadvantage that the starting material 3-aminopropane thiol hydrochloride is expensive and the yield by route A is only moderate.

Route A suffers from the disadvantage that the starting material 3-aminopropane thiol hydrochloride is expensive and the yield by this route is only moderate.

Although the starting material for Route B, tetrahydro-1,3-thiazine-2-thione, is relatively inexpensive the ethyl nitroacetate required in the second stage of the synthesis is not available in commercial quantities and this rules out this procedure for manufacturing on an industrial scale.

According to the present invention there is provided a method for the preparation of a thiazine derivative of the formula where each R is hydrogen or an appropriate aromatic or aliphatic substituent and X is hydrogen, halogen or lower alkyl, the method comprising reacting together a sulphur donor, a compound of the formula $Y_2C=CX-NO_2$ where Y is halogen (preferably chlorine) or another appropriate leaving group and a compound of the formula $$H_2NCR_2CR_2CR_2OSO_3H$$

Preferably, each R is independently hydrogen or lower alkyl and more preferably each R is hydrogen.

The sulphur donor may be any suitable source of sulphur, for example, sulphur itself, a sulphide, a hydrosulphide or hydrogen sulphide. Preferably, the sulphur donor is an ammonium or alkali metal sulphide or hydrosulphide, for instance, the alkali metal sulphide sodium sulphide.

A preferred method in accordance with the present invention may be represented as follows $$H_2NCH_2CH_2CH_2OSO_3H + Na_2S + Cl_2C=CHNO_2 \longrightarrow$$

$$HN\underset{\underset{CHNO_2}{\|}}{\diagup\!\!\!\diagdown}S$$

The starting aminopropylsulphate is easily prepared from 3-amino-propanol and sulphuric acid. The preferred reaction referred to above proceeds at room temperature and this would appear to rule out a reaction mechanism involving the formation of the aminopropanethiol since it is known that the formation of the thiol only occurs at an appreciable rate at temperatures greater than 80° C. It may be that the reaction mechanism involves an initial attack by the sulphide anion on the nitroethene in a Michael type addition. The resultant thiol anion may then displace the sulphate ion in the aminopropyl sulphate. Ring closure with the elimination of two molecules of hydrogen chloride then occurs to give the product.

Because of the insolubility of the dihalonitroethylene in water it is preferred to use a cosolvent. Preferably, the cosolvent is a water immiscible organic solvent such as benzene, toluene or ethylene dichloride.

Preferably, the reaction is conducted at a temperature in the range from 0°–80° C. although products formed at the higher temperatures are relatively more contaminated and more difficult to purify.

EXAMPLE

An example of a method in accordance with the present invention will now be described, by way of example only.

To a stirred flask fitted with a condensor were charged water (200 ml), toluene (200 ml), aminopropyl sulphate (100 gms), sodium sulphide (78 gms/60% active) and 1,1-dichloro-2-nitro ethylene (81.1 gms). The mixture was heated to 60° C. and the pH maintained between 6-8 by gradual addition of sodium hydroxide solution to absorb the hydrochloric acid liberated.

When the reaction was complete (about 1 hour) the reaction solution was cooled, the aqueous layer separated off and the pH adjusted to 5.5 with acetic acid.

The aqueous layer was then extracted with methylene chloride (3 times 100 ml). The methylene chloride was distilled out and the product recrystallised from isopropanol to give tetrohydro-2-(nitro methylene)-2H-1,3-thiazine having a melting point of 73°-76° C.

We claim:

1. A method for the preparation of a thiazine derivative of the formula

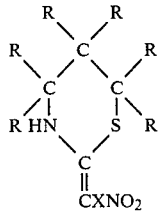

where each R is independently hydrogen or lower-alkyl and X is hydrogen, halogen or lower alkyl, which comprises reacting a sulphur donor, a compound of the formula $Y_2C=CXNO_2$ where Y is halogen or another leaving group and a compound of the formula $$H_2NCR_2CR_2CR_2OSO_3H.$$

2. A method according to claim 1 wherein the sulphur donor is an ammonium or alkali metal sulphide or hydrosulphide.

3. A method according to claim 1 wherein the sulphur donor is sodium sulphide.

4. A method according to claim 1 wherein Y is chlorine and X is hydrogen.

5. A method according to claim 1 wherein the reaction is conducted in the presence of water and a cosolvent immiscible with water.

6. A method according to claim 5 wherein the cosolvent is benzene, toluene or ethylene dichloride.

7. A method for the preparation of a compound of the formula

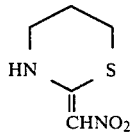

which comprises reacting sodium sulphide, a compound of the formula $Cl_2C=CHNO_2$ and a compound of the formula $$H_2NCH_2CH_2CH_2OSO_3H.$$

8. A method according to claim 1 wherein Y is chlorine.

* * * * *